United States Patent [19]

Viout et al.

[11] 4,129,711

[45] Dec. 12, 1978

[54] POLYMERS COMPRISING VINYL ESTERS-CROTONIC ACID

[75] Inventors: Andre Viout; Regine Pasero, both of Paris, France

[73] Assignee: L'Oreal, Paris, France

[21] Appl. No.: 601,017

[22] Filed: Aug. 1, 1975

Related U.S. Application Data

[60] Division of Ser. No. 309,502, Nov. 24, 1972, Pat. No. 3,925,542, which is a continuation-in-part of Ser. No. 747,470, Jul. 25, 1968, Pat. No. 3,716,633, which is a continuation-in-part of Ser. No. 655,770, Jul. 28, 1967, Pat. No. 3,579,629, which is a continuation-in-part of Ser. No. 530,395, Feb. 28, 1966, abandoned.

[30] Foreign Application Priority Data

| Mar. 3, 1965 [FR] | France | 65.7787 |
| Jan. 27, 1966 [FR] | France | 66.47441 |
| Aug. 3, 1966 [FR] | France | 66.71998 |
| Jul. 28, 1967 [LU] | Luxembourg | 54202 |

[51] Int. Cl.² .................. C08F 4/34; C08F 20/04; C08F 220/04; C08F 28/04

[52] U.S. Cl. .................. 526/286; 260/29.6 TA; 260/33.4 R; 526/16; 526/42; 526/52.3; 526/200; 526/218; 526/232; 526/289; 526/292; 526/317

[58] Field of Search .............. 526/317; 260/29.6 TA, 260/79.3 M, 79.3 R, 79.5 C, 78.30 A; 424/47

[56] References Cited

U.S. PATENT DOCUMENTS

| 3,231,534 | 1/1966 | Blades et al. | 260/29.6 TA |
| 3,282,879 | 11/1966 | Werner | 260/29.6 TA |
| 3,342,765 | 9/1967 | Oosterhof | 260/29.6 TA |
| 3,370,031 | 2/1968 | Grommers et al. | 260/29.6 TA |
| 3,455,887 | 7/1969 | Levine | 260/29.6 TA |
| 3,484,420 | 12/1969 | Chihara | 260/29.6 TA |
| 3,503,916 | 3/1970 | Warson et al. | 260/29.6 TA |
| 3,577,517 | 5/1971 | Kubot et al. | 424/47 |
| 3,755,237 | 8/1973 | Isaacs et al. | 260/29.6 TA |
| 3,759,858 | 5/1973 | Corey et al. | 260/29.6 TA |
| 3,810,977 | 5/1974 | Levine et al. | 260/29.6 TA |

FOREIGN PATENT DOCUMENTS

860677 2/1961 United Kingdom.

*Primary Examiner*—Herbert J. Lilling
*Attorney, Agent, or Firm*—Cushman, Darby & Cushman

[57] ABSTRACT

Copolymers of vinyl acetate, crotonic acid and an unsaturated ester or ether are employed in cosmetic compositions for the hair.

9 Claims, No Drawings

POLYMERS COMPRISING VINYL ESTERS-CROTONIC ACID

This is a division, of application Ser. No. 309,502 filed Nov. 24, 1972, now U.S. Pat. 3,925,542, which is a CIP of S.N. 747,470, filed July 25, 1968, now U.S. Pat. 3,716,633, which is a CIP of S.N. 655,770 filed July 28, 1967, now U.S. Pat. No. 3,579,629 and S.N. 530,395, filed Feb. 28, 1966, now abandoned.

Both natural and synthetic resins, usually in an aqueous or an aqueous alcoholic solution, are in current use as hair lacquers or hair-setting lotions.

The object of such use is to hold the coiffure in a desired shape and improve its appearance, particularly by imparting a desirable sheen thereto.

Among the resins heretofore used for this purpose are homopolymers such as polyvinylpyrrolidone, copolymers such as a vinylpyrrolidone/vinyl acetate copolymer, acrylic ester/unsaturated monoethylene acetate copolymers, esterified or amidified vinyl alkyl ether/maleic anhydride copolymers, as well as copolymers of vinyl acetate and unsaturated monoethylene acids such as crotonic acid.

The present invention relates to new copolymers which make it possible to prepare cosmetic compositions of better quality than those heretofore known.

The copolymers according to the invention make it possible to prepare hair lacquers or setting lotions which form films which hold the coiffure in shape much better than those made from the resins heretofore used.

Moreover, the use of these polymers results in a much more rapid hardening of the coating formed thereby, so that in order to provide a given shape-holding power it is necessary to use less than half as much of the polymer according to the invention as would be necessary if a known vinyl acetate/crotonic acid polymer, for example, were used.

It follows that cosmetic compositions according to the invention yield excellent results at a lower cost.

The copolymers according to the invention also impart other valuable properties to cosmetic compositions containing them.

They make it possible to produce films having a brighter sheen than the copolymers presently in use.

Moreover, they have a definite affinity for the hair, which has not only the advantage of causing the coiffure to hold its shape longer, when the new copolymers are used in setting lotions, but also that of permitting the hair to be combed without serious damage to the film formed by the copolymer. It is well known that when conventional resins are employed, combing almost completely removes those resins, which fall out in the form of a white powder. In the case of the copolymer according to the invention, on the contrary, combing is possible, even though the films formed by the copolymer may be easily removed by brushing or shampooing.

It is a further advantage of cosmetic compositions according to the invention that the film formed thereby is not very hygroscopic so that coiffures to which they have been applied retain their shape well even in a humid atmosphere.

Practically none of the products used hitherto is entirely satisfactory. The reason for this is that it is difficult simultaneously to achieve all the different characteristics which are desired in a lacquer or in a wave setting lotion, because these characteristics are often contradictory.

Thus it is desirable to be able to obtain a resin film on the hair which lasts well, has high brilliance and good lacquering power, but which at the same time adheres well to the hair and which has no marked tendency to flake. Furthermore the resin film, on the one hand, should not have significant hygroscopicity, otherwise the hair will become sticky in appearance, but, on the other hand, should be readily removable from the hair, by gentle brushing or by washing with any desired shampoo.

The cosmetic compositions known heretofore have had to have a compromise selection of the various desired properties, none of the known compositions effectively possessing all of the desired properties. Thus, in the past, certain properties have been deliberately chosen at the expense of other desirable properties. For example, some of the polymers used are very soluble in water. This avoids flaking of the film and allows the polymers to be easily removed by shampooing, but the polymers take up moisture and the hair rapidly becomes sticky. On the other hand, there have also been used resins which are much less hygroscopic but which give rise to the formation of white-colored scurf which is unaesthetic and which is difficult to remove with certain shampoos; furthermore these resins do not impart all the desired brilliance to the hair.

The applicants, after considerable work, have succeeded in providing new synthetic resins capable of being used in alcohol or aqueous alcoholic solutions as hair lacquers or hair wave setting lotions, these resins allowing each of the desirable properties indicated above to be simultaneously achieved to a considerable extent. Lotions or lacquers based on the new resins have improved properties which are readily noticeable during use, without any known defects being accentuated. Furthermore the new resins have the great advantage of being very easily removed from the hair by washing either by anionic or by cationic shampoos.

The present invention provides a new industrial product which comprises a copolymer obtained by copolymerization of vinyl acetate, crotonic acid, and at least one other polymerizable monomer.

More particularly, one embodiment of the present invention relates to a copolymer having a molecular weight ranging between 10,000–300,000 and preferably between 15,000–160,000 consisting essentially of (1) 75–85% by weight vinyl acetate, (2) 5–15% by weight crotonic acid and (3) 5–15% by weight of a monomer selected from the group consisting of (i) an ester of the formula,

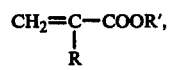

$$CH_2 = C - COOR',$$
$$|$$
$$R$$

wherein R is selected from the group consisting of hydrogen and methyl, and R' is selected from the group consisting of methyl, butyl, ethylhexyl, butoxyethyl and lauryl, and (ii) an ether of the formula, $CH_2 = CH - O - R''$ wherein $R''$ is selected from the group consisting of ethyl, isopropyl, butyl, isobutyl and chloroethyl.

In this embodiment the said ester can be selected from the group consisting of methyl acrylate, butylacrylate, ethylhexyl acrylate, lauryl acrylate, methyl methacrylate, butyl methacrylate, butoxyethyl methacrylate and lauryl methacrylate. The said ether can be selected from the group consisting of isopropyl vinyl ether, isobutyl vinyl ether and chloroethyl vinyl ether.

In another embodiment of the present invention, there is provided a copolymer having a molecular weight ranging between 10,000–300,000 and preferably between 15,000–160,000, said copolymer consisting essentially of (1) 63–88% by weight vinyl acetate, (2) 5–15% by weight crotonic acid, (3) 5–25% by weight of a monomer selected from the group consisting of (i) vinylic ester of the formula, R — COO — CH = CH$_2$ wherein R is a linear or branched chain hydrocarbon containing 10–22 carbon atoms and (ii) allylic or methallylic ester of the formula

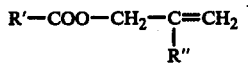

wherein R' is a linear or branched chain hydrocarbon containing 10–22 carbon atoms and R" is selected from the group consisting of hydrogen and methyl.

In this embodiment the vinylic ester can be selected from the group consisting of vinyl laurate, vinyl palmitate, vinyl stearate, vinyl isostearate and vinyl behenate. The said allylic or methallylic ester can be selected from the group consisting of allyl laurate, methallyl laurate, allyl stearate, methallyl stearate, allyl isostearate, methallyl isostearate and allyl behenate.

In yet another embodiment of the present invention, there is provided a copolymer having a molecular weight ranging between about 10,000–300,000, preferably between about 15,000–160,000, said copolymer consisting essentially of (1) 50–90% by weight of a monomer selected from the group consisting of vinyl acetate, vinyl propionate, allyl acetate and vinyl butyrate, (2) 5–25% by weight of a monomer selected from the group consisting of crotonic acid, 3-butenoic acid, 4-pentenoic acid, allylmalonic acid, allyloxyacetic acid and allyloxpropionic acid, and (3) 5–30% by weight of a monomer selected from the group consisting of lanolin crotonate, oleyl crotonate, 1-allyloxy-3-dodecyloxy-2-propanol, 1-allyloxy-3-dodecylthio-2-propanol, 1-octene, 1-hexadecene, allyl oleate, stearyl vinyl ether and an ester of the formula,

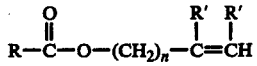

wherein R in linear alkyl having 8–18 carbon atoms, n is 0–1 and R' is selected from the group consisting of hydrogen and methyl.

In this embodiment the said ester can be selected from the group consisting of allyl stearate, vinyl laurate, crotyl laurate, allyl laurate, vinyl stearate and vinyl octanoate.

In order to use the copolymers of the invention in hair lacquers or wave setting lotions it is necessary to form salts thereof by means of mineral or organic bases, so as to render copolymers soluble both in water and in organic solvents, especially in the halogenated hydrocarbons currently used as aerosol propellants. Illustrative suitable bases include ammonia, mono, di and tri ethanolamine, monoethylamine, dimethylamine, diethylamine, aminoethylamine, monoisopropanolamine, 2-amino-2-methyl-propanol-1, 2-amino-2-methyl-propanediol-1,3 and morpholine. The amounts of base used may vary between rather wide limits, for example between 10 and 150% and preferably 50 to 100% relative to the theoretical amount required for neutralization, without affecting the desired result. Advantageously, an equimolecular quantity of the base relative to the amount of crotonic acid contained in the copolymer is used.

The present invention therefore also includes a cosmetic composition essentially characterized by the fact that they contain 1–4 weight percent at least one salt of a copolymer of the invention in an alcoholic or aqueous alcoholic solution having a pH of 2.5 to 10.

The cosmetic product of the invention may for example be a hair lacquer obtained by dissolving one or several salts of the copolymers of the invention in a lower alkanol, such as ethanol or isopropanol, or an aqueous solution of said lower alkanol. Suitably, this alcoholic solution, mixed with a propellant gas liquified under pressure, is charged into an aerosol container. For example, an aerosol lacquer of the invention may be obtained by adding, to a mixture consisting of 25 to 33 parts by weight of an anhydrous aliphatic alcohol such as ethanol or isopropanol and 66 to 75 parts by weight of a propellant gas or a mixture of propellant gases such as halogenated hydrocarbons, 1 to 4% by weight of one or several salts of copolymers of the invention.

The cosmetic product of the invention may also for example be a wave setting lotion obtained by dissolving, in an aqueous alcoholic solution containing 20 to 70% of alcohol, 1 to 3% by weight of the solution of a salt of a copolymer, or of a mixture of salts of copolymers of the invention.

It is to be understood that auxiliary materials such as plasticizers, perfumes, dyestuffs or any other auxiliary agent normally used in cosmetics, may be added if desired to the cosmetic products of the invention. Representative of such auxiliary materials or components are lanolin derivatives, such as Solutan and Acetulan of the American Chloresterol Corp., Lantrol AWS (Malmstron Chemical Corp.), polyethylene glycol (Gafanol of the GAF), dipropyleneglycol, glycerol, silicone solvents (Fluid 470, Dow Corning), castor oil, dibutyl phthalate, etc. Known hair dyes such as D and C Red No. 5, FDC Green No. 3, D and C Yellow 10, FDC Blue 1, 2,4-dinitro-6-aminophenol, 4-nitro 1,2-phenylenediamine and 1-hydroxy-2-amino-5-nitrobenzene.

The copolymers of the invention are of great interest when used in the cosmetic field because they have very good film-forming properties, they are not sensitive to the effect of humidity, and they leave the hair very glossy. Furthermore it is remarkable that they can be easily removed by brushing or washing and that they have no tendency to scurf when applied to hair.

The precise proportions, relative to vinyl acetate, of the crotonic acid and of the other monomer depend upon the particular desired cosmetic application. The following discussion illustrates the factors to be taken into account.

A reduction of the proportion of crotonic acid in the copolymer results in a reduction of the solubility of the copolymer salt in water or in alcohol, which can limit its possible application and renders its removal by washing more difficult. On the other hand, if the proportion of crotonic acid in the copolymer is excessively increased the copolymer salt tends to become sticky, in proportion to the increase in its hygroscopicity. Also, an increase in the proportion of ester and/or ether results in an increase of the hardness of the copolymer salt and it tends to become insoluble in water. Conversely, if the amount of ester and/or ether is decreased then the gloss and the hardness of the film covering the hair is simultaneously diminished.

The copolymers of the invention have the important advantage over known copolymers of having a smaller "moisture regain" when placed in a humid air environment. In order to demonstrate this characteristic the applicants have carried out comparative measurements of moisture regain of two films in an atmosphere of 81.5% relative humidity.

The first film consisted of a copolymer of the invention having the composition:

| | |
|---|---|
| vinyl acetate | 80% |
| crotonic acid | 10% |
| methyl methacrylate | 10% |

The second film consisted of a commercially available copolymer having the composition:

| | |
|---|---|
| vinyl acetate | 90% |
| crotonic acid | 10% |

The percentage humidity regain at equilibrium is 17.8% for the copolymer of the invention and 22.8% for the other copolymer. There is thus a practical improvement in the hygroscopicity of the film of about 20%.

The copolymers of the invention may be prepared by various methods such as bulk polymerization, solution polymerization or suspension polymerization in solvents such as alcohols or benzene. Suspension polymerization is preferred, however, as it enables the copolymer to be obtained in the form of beads which are easily separated off, washed and dried.

Polymerization in suspension which permits obtaining the copolymer in the form of fine particles is effected in water in the presence of a protective colloid such as polyvinylic alcohol, or polyacrylic acid (product known as Carbopol) or hydroxyethylcellulose (sold under the trademark Cellosize).

When the polymerization is carried out in suspension in water, in the presence of a protective colloid, a catalyst and a chain length regulator, about 2 to 3 parts by weight of the monomers are used for 4 to 5 parts by weight of water. The concentration of protective colloid may vary for example between 0.06% and 1% relative to the weight of the aqueous phase.

The catalysts may be used in proportions of 1 to 5% by weight and preferably 1.5 to 3% by weight relative to the monomers. Suitable catalysts include benzoyl peroxide, lauryl peroxide and azobisisobutyronitrile.

Suitable chain length regulators, include butylmercaptan or laurylmercaptan, which may be used in concentrations of about 0.25 to 0.70% by weight relative to the monomers used.

The following non-limitative Examples further illustrate the invention.

EXAMPLE 1

Preparation of a copolymer of 80% vinyl acetate, 10% crotonic acid and 10% methyl methacrylate.

1800 g. of an aqueous solution containing 0.06% of Carbopol (neutralized to pH 7 by N/2 NaOH) are placed in a 6 liter flask fitted with a stirrer, a reflux condenser, a thermometer and a nitrogen inlet tube.

After flushing with nitrogen the following mixture of monomers is introduced with stirring:

960 g. of vinyl acetate
120 g. of methyl methacrylate
120 g. of crotonic acid
22.2 g. of azobisisobutyronitrile
8.4 g. of laurylmercaptan The mixture is heated to reflux with stirring while constantly maintaining the flow of nitrogen. The temperature remains at 69° for about 4 hours and then rises progressively to 90°. This temperature is maintained for one hour in order to complete the polymerization and the mixture then is deodorized by removing the residual monomers. After cooling, the product is filtered off, washed and dried, initially at room temperature and subsequently at 50°. The copolymer is obtained in the form of transparent beads in a yield of 86%. Molecular weight: 55,000. Acid value = 64.

EXAMPLE 2

Preparation of a copolymer of 80% vinyl acetate, 10% crotonic acid, and 10% isobutyl vinyl ether.

7500 g. of a 1% aqueous solution of Cellosize (hydroxyethylcellulose) are placed in a 20 liter glass reactor equippped with an anchor-shaped stirrer, a reflux condenser, a thermometer and nitrogen inlet tube. The solution is purged with a current of nitrogen and the following monomer mixture is introduced with stirring:

| | |
|---|---|
| vinyl acetate | 2,400 g. |
| isobutyl vinyl ether | 300 g. |
| crotonic acid | 300 g. |
| azobisisobutyronitrile | 45 g. |
| laurylmercaptan | 7.5 g |

The duration of the polymerization, carried out as in Example 1, is of the order of 11 to 12 hours.

After filtering, washing and drying, the copolymer is obtained in the form of beads in a yield of 77%. Molecular weight: 45,000. Acid value = 66.

EXAMPLE 3

Preparation of a copolymer of 75% vinyl acetate, 10% crotonic acid, 10% isobutyl vinyl ether, and 5% lauryl methacrylate.

The desired copolymer is obtained in a yield of 75% under the same conditions as those described in Example 2, by copolymerizing 75 g. of vinyl acetate, 10 g. of crotonic acid, 10 g. of isobutyl vinyl ether and 5 g. of lauryl methacrylate. Molecular weight: 35,000. Acid value = 67.

EXAMPLE 4

Preparation of a copolymer of 83% vinyl acetate, 10% methyl methacrylate and 7% crotonic acid.

400 g. of an 0.06% aqueous solution of Carbopol (neutralized to pH 7 by means of N/2 caustic soda) are placed in a flask equipped with a stirrer, a reflux condenser, a thermometer and a nitrogen inlet tube.

After flushing with nitrogen the following mixture is introduced with stirring:

| | |
|---|---|
| vinyl acetate | 249 g. |
| methyl methacrylate | 30 g. |
| crotonic acid | 21 g. |
| azobisisobutyronitrile | 2.35 g. |
| lauryl peroxide | 2.35 g. |
| butylmercaptan | 1.4 g. |

The mixture is heated to reflux under nitrogen, with stirring. The temperature rises to 90°-92°, after having remained at a 68° stage for 4 hours.

When the polymerization is complete the mixture is cooled and the product filtered off, washed and dried.

The copolymer is obtained in the form of transparent beads, in a yield of 70%. Molecular weight: 50,000. Acid value = 50.

EXAMPLE 5

Preparation of a copolymer of 84% vinyl acetate, 6% lauryl methacrylate, 3% lauryl acrylate and 7% crotonic acid.

400 g. of an aqueous 0.06% Carbopol solution (neutralized to pH 7 by means of N/2 caustic soda) are introduced into a flask fitted with a stirrer, a reflux condenser, a thermometer and a nitrogen inlet tube.

The solution is purged with nitrogen and the following mixture introduced with stirring.

| | | |
|---|---|---|
| vinyl acetate | 252 g. | |
| lauryl methacrylate | 18 g. | |
| lauryl acrylate | 9 g. | |
| crotonic acid | 21 g. | |
| azobisisobutyronitrile | 2.35 g. | |
| lauryl peroxide | 2.35 g. | |
| laurylmercaptan | 0.9 g. | |

The mixture is heated to reflux. The polymerization is complete after about 10 hours.

After cooling the product is filtered off, washed and dried. The copolymer is obtained in the form of beads in a yield of 86%. Molecular weight: 85,000. Acid value = 49.

EXAMPLE 6

Preparation of a copolymer of 80% vinyl acetate, 5% methyl methacrylate, 5% methyl acrylate and 10% crotonic acid.

600 g. of an 0.06% aqueous solution of Carbopol (neutralized to pH 7 by N/2 strength caustic soda) are placed in a flask fitted with a stirrer, a reflux condenser, a thermometer and a nitrogen inlet tube.

The solution is purged with nitrogen and the following mixture introduced with stirring.

| | | |
|---|---|---|
| vinyl acetate | 320 g. | |
| methyl acrylate | 20 g. | |
| methyl methacrylate | 20 g. | |
| crotonic acid | 20 g. | |
| azobisisobutyronitrile | 7.4 g. | |
| laurylmercaptan | 0.25 g. | |

After polymerization, transparent beads are obtained in a yield of 80%. Molecular weight: 60,000. Acid value = 67.

EXAMPLE 7

Preparation of a copolymer of 75% vinyl acetate, 10% methyl methacrylate, 5% lauryl methacrylate and 10% crotonic acid.

The desired copolymer is obtained in a yield of 78% under the same conditions as those described in Example 6, by copolymerizing 300 g. of vinyl acetate, 40 g. of methyl methacrylate, 20 g. of lauryl methacrylate and 40 g. of crotonic acid in the presence of 0.8 g. of azobisisobutyronitrile. Molecular weight: 140,000. Acid value = 68.

EXAMPLE 8

Preparation of a copolymer of 84% vinyl acetate, 6% butyl methacrylate, 3% butyl acrylate and 7% crotonic acid.

The desired copolymer is obtained in a yield of 68% under the same conditions as those described in Example 4, by copolymerizing 252 g. of vinyl acetate, 18 g. of butyl methacrylate, 9 g. of butyl acrylate and 21 g. of crotonic acid in the presence of 0.7 g. of azobisisobutyronitrile. Molecular weight: 175,000. Acid value = 51.

EXAMPLE 9

Preparation of a copolymer of 84% vinyl acetate, 6% lauryl methacrylate, 3% methyl methacrylate and 7% crotonic acid.

The desired copolymer is obtained in a yield of 65% under the same conditions as those described in Example 4, by copolymerizing 252 g. of vinyl acetate, 18 g. of lauryl methacrylate, 9 g. of methyl methacrylate and 21 g. of crotonic acid in the presence of 6 g. of azobisisobutyronitrile. Molecular weight: 80,000. Acid value = 50.

EXAMPLE 10

Preparation of a copolymer of 80% vinyl acetate, 10% of 2-ethylhexyl acrylate and 10% crotonic acid.

600 g. of an aqueous 0.06% solution of Carbopol (neutralized to pH 7 by means of N/2 caustic soda) are introduced into a flask fitted with a stirrer, a reflux condenser, a thermometer and a nitrogen inlet tube.

The solution is purged with nitrogen and the following monomer mixture is added with stirring.

| | | |
|---|---|---|
| vinyl acetate | 240 g. | |
| 2-ethylhexyl acrylate | 30 g. | |
| crotonic acid | 30 g. | |
| azobisisobutyronitrile | 2.6 g. | |
| lauryl peroxide | 2.6 g. | |
| lauryl mercaptan | 1.4 g. | |

The polymerization is complete at the end of 11 hours of heating. The desired copolymer is obtained in a yield of 75%. Molecular weight: 80,000. Acid value = 66.

EXAMPLE 11

Preparation of a copolymer of 80% vinyl acetate, 10% of lauryl methacrylate and 10% of crotonic acid.

The desired copolymer is obtained in a yield of 85% under the same conditions as those described in Example 10, by copolymerizing 240 g. of vinyl acetate, 30 g. of lauryl methacrylate and 30 g. of crotonic acid in the presence of 15 g. of azobisisobutyronitrile. Molecular weight: 20,000. Acid value = 68.

EXAMPLE 12

Preparation of a copolymer of 75% vinyl acetate, 10% of methyl methacrylate, 5% of lauryl methacrylate and 10% of crotonic acid.

The desired copolymer is obtained in a yield of 84% by working under the same conditions as those described in Example 6, but with 800 g. of the aqueous phase instead of 600 g. in the presence of 2 g. of azobisisobutyronitrile. Molecular weight: 70,000. Acid value = 65.

EXAMPLE 13

Preparation of a copolymer of 80% vinyl acetate, 10% of butoxyethyl methacrylate and 10% of crotonic acid.

450 g. of a 1% aqueous solution of Cellosize are introduced into a flask fitted with a stirrer, a reflux condenser, a thermometer and a nitrogen inlet tube.

The solution is purged by means of a stream of nitrogen and the following mixture of monomers introduced with stirring:

| | |
|---|---|
| vinyl acetate | 160 g. |
| butoxyethyl methacrylate | 20 g. |
| crotonic acid | 20 g. |
| azobisisobutyronitrile | 3.7 g. |
| laurylmercaptan | 0.6 g |

The mixture is heated to reflux point with stirring. The duration of the polymerization is of the order of 11 hours.

After cooling the copolymer is filtered off, washed and dried. The desired polymer is obtained in the form of transparent beads, in a yield of 70%. Molecular weight: 60,000. Acid value = 66.

EXAMPLE 14

Preparation of a copolymer of 80% vinyl acetate, 10% chloroethyl vinyl ether and 10% of crotonic acid.

The desired copolymer is obtained in a yield of 73% under the same conditions as those described in Example 12, by copolymerizing 160 g. of vinyl acetate, 20 g. of chloroethyl vinyl ether and 20 g. of crotonic acid in the presence of 4 g. of benzoyl peroxide. Molecular weight: 65,000. Acid value = 67.

EXAMPLE 15

Preparation of copolymer in suspension: vinyl acetate 75% crotonic acid 10%, vinyl stearate 15%.

There is placed in a vessel fitted with an agitator, a reflux refrigerant, a thermometer, and a nitrogen conveying tube, 400 grams of an aqueous hydroxyethylcellulose solution known under the trademark Cellosize at 1% concentration.

| | |
|---|---|
| vinyl acetate | 225 g. |
| crotonic acid | 30 g. |
| vinyl stearate | 45 g. |
| azobisisobutyronitrile | 3.75 g. |

It is brought to reflux with stirring and under nitrogen. After about 8 hours the polymerization is ended.

It is allowed to cool, dried in air, and heat dried. The copolymer is obtained which is in the form of fine particles with a yield of 85%. Molecular weight: 80,000. Acid value = 69.

By way of example and to show the weak hygroscopicity of polymers according to the invention, there will be prepared in identical manner three films to be placed for 24 hours in an atmosphere having a relative humidity of 80%, after which is measured the quantity of water absorbed with respect to the initial weight of the film.

The first film which is constituted by a polyvinylpyrrolidone/vinyl acetate copolymer took up 28% of water.

The second film which is constituted by a vinyl acetate/crotonic acid copolymer absorbed 15% of water.

Finally, the third copolymer which is that described in the preceding example, took up only 11% of water.

Thus it is seen that it presents a weak hygroscopicity with respect to the other known polymers.

EXAMPLE 16

Preparation of a copolymer in mass of vinyl acetate 80%, crotonic acid 10%, vinyl stearate 10%.

There is placed in a 500 cc reactor fitted with an agitator, thermometer, reflux refrigerant and nitrogen supply tube, the following mixture of monomers:

| | |
|---|---|
| vinyl acetate | 160 g. |
| crotonic acid | 20 g. |
| vinyl stearate | 20 g. |
| benzoyl peroxide | 2.35 g. (85% pure) |

The above mixture is heated at reflux under agitation and under nitrogen.

In the course of polymerization the mixture thickens and when polymerization is terminated, after 5 or 6 hours, the polymer appears in the form of a solid mass which is evacuated hot.

Through cooling there is obtained, with a quantitative yield, a yellow colored transparent product which can be reduced to a powder. Molecular weight: 70,000. Acid value = 68.

EXAMPLE 17

Preparation of a copolymer in mass of 70% vinyl acetate, 10% crotonic acid, 20% vinyl stearate.

The procedure is the same as described in Example 16.

In the same way a quantitative yield of a light yellow colored transparent product is obtained which can be easily powdered. Molecular weight: 68,000. Acid value = 68.

EXAMPLE 18

Preparation of a copolymer in mass of 75% vinyl acetate, 10% crotonic acid, 15% allyl stearate.

The procedure is the same as that of Example 16.

A quantitative yield of an easily powdered transparent product is obtained. Molecular weight: 60,000. Acid value = 68.

EXAMPLE 19

Preparation of a copolymer in mass of 75% vinyl acetate, 10% crotonic acid, 15% vinyl stearate.

The procedure is the same as that of Example 16.

A quantitative yield of an easily powdered transparent product is obtained. Molecular weight: 62,000. Acid value = 68.

EXAMPLE 20

Preparation of a particulate copolymer of 71.5% vinyl acetate, 8.5% crotonic acid, 20% vinyl laurate.

The procedure is the same as that described in Example 15 but the catalyst is replaced by 0.2 g. of benzoyl peroxide.

An 85% yield of the desired copolymer is obtained. Molecular weight: 170,000. Acid value = 53.

EXAMPLE 21

Preparation of a particulate copolymer, 75% vinyl acetate, 10% crotonic acid, 15% allyl laurate.

The procedure is the same as described in Example 15, but the catalyst is replaced by 5 g of benzoyl peroxide.

A 75% yield of the desired polymer is obtained. Molecular weight: 20,000. Acid value = 68.

EXAMPLE 22

Preparation of a particulate copolymer of 75% vinyl acetate, 10% crotonic acid, 15% allyl isostearate.

The procedure is the same as that described in Example 15, but the catalyst is replaced by 2 g. of azobisisobutyronitrile.

A 63% yield of the desired copolymer is obtained. Molecular weight: 60,000. Acid value = 69.

EXAMPLE 23

Preparation of a particulate copolymer of 75% vinyl acetate, 10% crotonic acid, 15% methallyl stearate.

The procedure is the same as that described in Example 15, but the catalyst is replaced by 2 g. of azobisisobutyronitrile.

A 62% yield of the desired copolymer is obtained. Molecular weight: 55,000. Acid value = 65.

EXAMPLE 24

Preparation of a particulate copolymer of 75% vinyl acetate, 10% crotonic acid, 15% vinyl isostearate.

The procedure is the same as that described in Example 15 but the catalyst is replaced by 3 g. of benzoyl peroxide.

A 75% yield of the desired copolymer is obtained. Molecular weight: 45,000. Acid value = 68.

EXAMPLE 25

Preparation of a granular copolymer comprising 70% vinyl acetate, 10% crotonic acid, 10% allyl stearate, 10% vinyl stearate.

The procedure is the same as in Example 15.

The result is a 75% yield of the desired copolymer in granular form. Molecular weight: 70,000. Acid value = 67.

EXAMPLE 26

Preparation of a bead or granular copolymer comprising 66.5% vinyl acetate, 8.5% crotonic acid and 25% vinyl laurate.

The procedure is the same as in Example 15, and a 72% yield of the desired copolymer is obtained. Molecular weight: 120,000. Acid value = 56.

EXAMPLE 27

Preparation of a copolymer in pellet form comprising 75% vinyl acetate, 10% 4-pentenoic acid, and 15% allyl stearate.

3,429 g. of an aqueous 1% solution of hydroxyethylcellulose sold under the trademark "Cellosize" is placed in a flask provided with agitating means, a reflux condenser, a thermometer and a tube for introducing nitrogen.

After bubbling in nitrogen, the following mixture is introduced while agitation is continued:

| | |
|---|---|
| vinyl acetate | 1929 g. |
| 4-pentenoic acid | 257 g. |
| allyl stearate | 386 g. |
| azobisisobutyronitrile | 32.15 g. |

This is brought to reflux under a nitrogen atmosphere while being subjected to agitation. After about 8 hours polymerization is complete. The product is permitted to cool and dried. The result is a copolymer in granular form and a yield of 75%. Molecular weight: 50,000. Acid value = 49.5.

EXAMPLE 28

Preparation of a granular copolymer comprising 70% vinyl acetate, 10% 4-pentenoic acid and 20% vinyl laurate.

The procedure is the same as in Example 27.

The result is a 72% yield of the desired copolymer in granular form.

Molecular weight: 58,000. Acid value = 50.

EXAMPLE 29

Preparation of a granular copolymer comprising 75% vinyl acetate, 10% 3-butenoic acid, and 15% allyl stearate.

The procedure is the same as in Example 27.

The result is a 70% yield of the desired copolymer. Molecular weight: 40,000. Acid value = 59.

EXAMPLE 30

Preparation of a granular copolymer comprising 71.5% vinyl acetate, 8.5% 3-butenoic acid, and 20% vinyl laurate.

The procedure is the same as in Example 27.

The result is a 60% yield of the desired copolymer. Molecular weight: 60,000. Acid value = 51.

EXAMPLE 31

Preparation of a granular copolymer comprising 80% vinyl acetate, 10% 4-pentenoic acid, and 10% stearyl vinyl ether.

The procedure is the same as in Example 27.

The result is an 80% yield of the desired copolymer. Molecular weight: 35,000. Acid value = 48.

EXAMPLE 32

Preparation of a granular copolymer comprising 71.5% vinyl acetate, 8.5% 4-pentenoic acid, and 20% vinyl laurate.

The procedure is the same as in Example 27.

The result is a 75% yield of the desired copolymer. Molecular weight: 62,000. Acid value = 42.

EXAMPLE 33

Preparation of a granular copolymer comprising 75% vinyl acetate, 10% crotonic acid, and 15% crotyl laurate.

The procedure is the same as in Example 27.

The result is a 60% yield of the desired copolymer. Molecular weight: 40,000. Acid value = 68.

EXAMPLE 34

Preparation of a granular copolymer comprising 75% vinyl acetate, 10% crotonic acid, 15% lanolin crotonate.

The procedure is the same as in Example 27.

The result is a 60% yield of the desired copolymer. Molecular weight: 35,000. Acid value = 69.

EXAMPLE 35

Preparation of a granular copolymer comprising 80% vinyl acetate, 10% crotonic acid, 10% stearylvinyl ether.

A quantitative yield of the desired copolymer is obtained.
Molecular weight: 40,000. Acid value = 55.

EXAMPLE 49

Preparation of a copolymer in the form of a continuous mass which comprises 75% vinyl propionate, 10% crotonic acid, and 15% allyl stearate.

The procedure is the same as in Example 45.

A quantitative yield of the desired copolymer is obtained.
Molecular weight: 70,000. Acid value = 69.

EXAMPLE 50

Preparation of a copolymer in the form of a continuous mass which comprises 75% vinyl propionate, 10% allyl oxyacetic acid and 15% allyl stearate.

The procedure is the same as in Example 45.

A quantitative yield of the desired copolymer is obtained.
Molecular weight: 65,000. Acid value = 41.

EXAMPLE 51

Preparation of copolymer in the form of a continuous mass comprising 37.5% vinyl acetate, 37.5% vinyl propionate, 10% allyloxyacetic acid and 15% allyl stearate.

The procedure is the same as in Example 45.

A quantitative yield of the desired copolymer results.
Molecular weight: 70,000. Acid value = 54.

EXAMPLE 52

Preparation of a granular copolymer comprising 70% vinyl acetate, 10% allyl acetate, 10% allyloxyacetic acid and 10% allyl stearate.

The procedure is the same as in Example 45.
A 78% yield of the desired copolymer results.
Molecular weight: 40,000. Acid value = 41.

EXAMPLE 53

Preparation of a copolymer in the form of a continuous mass comprising 77.5% vinyl acetate, 7.5% allyloxyacetic acid and 15% allyl stearate.

The procedure is the same as in Example 45.
A quantitative yield of the desired copolymer results.
Molecular weight: 90,000. Acid value = 38.

EXAMPLE 54

Preparation of a granular copolymer comprising 71.5% vinyl acetate, 8.5% 1-pentenoic acid and 20% vinyl stearate.

The procedure is the same as in Example 45.
A 68% yield of the desired copolymer is obtained.
Molecular weight: 70,000. Acid value = 43.

EXAMPLES OF APPLICATION

EXAMPLE 55

A solution having the following composition is prepared for use as an aerosol hair lacquer:

| | |
|---|---|
| copolymer described in Example 31 | 8 g. |
| diisopropylamine | 0.693 g. |
| perfume | 0.30 g. |
| absolute ethyl alcohol q.s.p. | 100 g. |

25 g. of this solution are introduced into an aerosol bomb with 47 g. of the product sold under the trademark Freon 11, trichloromonofluoromethane and 28 g. of the product sold under the trademark Freon 12, dichlorodifluoromethane.

When this is expelled as a spray it serves as a shiny non-hygroscopic lacquer.

EXAMPLE 56

A solution having the following composition is prepared for use as an aerosol hair lacquer:

| | |
|---|---|
| copolymer described in Example 31 | 6 g. |
| diisopropylamine | 0.462 g. |
| butyl palmitate | 0.25 g. |
| perfume | 0.30 g. |
| isopropyl alcohol, q.s.p. | 100 g. |

30 g. of this solution are introduced into an aerosol bomb together with 50 g. of the product sold under the trademark Freon 11 and 20 g. of the product sold under the trademark Freon 12.

This composition is particularly suitable for use as a hair lacquer.

EXAMPLE 57

A solution having the following composition is prepared for use as a hair-setting lotion:

| | |
|---|---|
| copolymer described in Example 28 | 1.8 g. |
| triethanolamine q.s.p. pH 7.4 | |
| isopropyl alcohol | 50 g. |
| water q.s.p. | 100 g. |

20 ml of this solution are applied to hair which has been washed and dried. It is noted that the hair then combs easily when damp. After drying, the lacquer and sheen are excellent. It combs easily and has excellent resilience.

EXAMPLE 58

The following composition is prepared for use as a hair-setting lotion:

| | |
|---|---|
| copolymer described in Example 30 | 2.5 g |
| di-ethanolamine, q.s.p. pH 7 | |
| ethyl alcohol | 60 g. |
| water, q.s.p. | 100 ml |

After application the results are excellent, particularly with respect to sheen, the absence of stickiness and manageability.

EXAMPLE 59

The following composition is prepared for use as a hair-setting lotion:

| | |
|---|---|
| copolymer described in Example 29 | 1.5 g. |
| 2-amino-2-methyl-1, 3-propanediol, q.s.p. pH 7.3 | |
| ethyl alcohol | 50 g |
| perfume | 0.1 g. |
| water, q.s.p. | 100 ml |

20 ml of this solution are applied to bleached hair which has first been washed and dried.

The procedure is the same as in Example 27.
The result is a 72% yield of the desired copolymer. Molecular weight: 32,000. Acid value = 68.

EXAMPLE 36

Preparation of a copolymer in lump form comprising 80% vinyl acetate, 10% crotonic acid and 10% 1-octene.

A mixture of the following monomers is introduced into a 500 cc reactor provided with agitating means, a thermometer, a reflux condenser and a tube for introducing nitrogen:

| vinyl acetate | 160 g. |
| crotonic acid | 20 g. |
| 1-octene | 20 g. |
| benzoyl peroxide | 2.35 g. (85% pure) |

This is heated to reflux while being agitated under a nitrogen atmosphere. The mixture thickens during polymerization and when polymerization is complete, after 5 to 6 hours, the polymer takes the form of a lump which is removed while warm.

After cooling, the end product is transparent, yellowish and may be ground up. Molecular weight: 70,000. Acid value = 71.

EXAMPLE 37

Preparation of a copolymer in lump form comprising 80% vinyl acetate, 10% crotonic acid and 10% 1-hexadecene.

The procedure is the same as in Example 36.
A quantitative yield of the desired copolymer results. Molecular weight: 70,000. Acid value = 71.

EXAMPLE 38

Preparation of a granular copolymer comprising 75% vinyl acetate, 10% crotonic acid and 15% allyl oleate.
The procedure is the same as in Example 27.
An 81% yield of the desired copolymer results. Molecular weight: 62,000. Acid value = 70.

EXAMPLE 39

Preparation of a granular copolymer comprising 75% vinyl acetate, 10% crotonic acid and 15% oleyl crotonate.
The procedure is the same as in Example 27.
The result is 70% yield of the desired copolymer. Molecular weight: 50,000. Acid value = 62.

EXAMPLE 40

Preparation of a granular copolymer comprising 80% vinyl acetate, 10% crotonic acid, 10% 1-allyloxy-3-dodecylthio-2-propanol.
The procedure is the same as in Example 27.
The result is a 74% yield of the desired copolymer in granular form. Molecular weight: 45,000. Acid value = 36.

EXAMPLE 41

Preparation of a granular copolymer comprising 80% vinyl acetate, 10% crotonic acid, 10% 1-allyloxy-3-dodecyloxy-2-propanol.
The procedure is the same as in Example 27.
The result is a 70% yield of the desired copolymer. Molecular weight: 45,000. Acid value = 72.

EXAMPLE 42

Preparation of a granular copolymer comprising 70% vinyl acetate, 10% crotonic acid, and 20% vinyl octanoate.
The procedure is the same as in Example 27.
The result is a 70% yield of the desired copolymer. Molecular weight: 72,000. Acid value = 72.

EXAMPLE 43

Preparation of a granular copolymer comprising 75% vinyl acetate, 10% allyloxyacetic acid, and 15% allyl stearate.
The procedure is the same as in Example 27.
The result is a 71% yield of the desired copolymer. Molecular weight: 60,000. Acid value = 53.

EXAMPLE 44

Preparation of a granular copolymer comprising 71.5% vinyl acetate, 8.5% allyloxyacetic acid and 20% vinyl laurate.
The procedure is the same as in Example 27.
The result is a 73% yield of the desired copolymer. Molecular weight: 110,000. Acid value = 34.

EXAMPLE 45

Preparation of a copolymer in a single mass comprising 75% vinyl acetate, 10% allyloxyacetic acid, and 15% allyl laurate.
The following mixture of monomers is placed in 2500 ml reactor equipped with agitating means, a thermometer, a reflux condenser, and a tube for introducing nitrogen.

| vinyl acetate | 112.5 g. |
| allyloxyacetic acid | 15 g. |
| allyl laurate | 22.5 g. |
| benzoyl peroxide | 1.9 g. |

This is heated to reflux under a nitrogen atmosphere. During the polymerization the mixture thickens. After 20 hours, polymerization ceases. Cooling then results in a quantitative yield of a light yellow product which can be ground up.
Molecular weight: 50,000. Acid value = 56.

EXAMPLE 46

Preparation of a copolymer in a continuous mass comprising 75% vinyl acetate, 10% allyloxypropionic acid and 15% allyl stearate.
The procedure is the same as in Example 45.
A quantitative yield of the desired copolymer is obtained.
Molecular weight: 65,000. Acid value = 48.

EXAMPLE 47

Preparation of a copolymer in the form of a continuous mass comprising 71.5% vinyl acetate, 8.5% allyloxypropionic acid and 20% vinyl laurate.
The procedure is the same as in Example 45.
An excellent yield of the desired copolymer is obtained. Molecular weight: 110,000. Acid value = 39.

EXAMPLE 48

Preparation of a copolymer in the form of a continuous mass comprising 75% vinyl acetate, 10% allyloxyacetic acid and 15% crotyl laurate.
The procedure is the same as in Example 45.

The results are excellent from the point of view of softness, sheen and holding power, even in humid weather.

EXAMPLE 60

A hair-setting lotion having the following composition is prepared:

| | |
|---|---|
| copolymer prepared as in Example 54 aminoethylpropanediol, q.s.p. 100% neutralization | 2 g. |
| Cetavlon (cetrimonium bromide) | 0.1 g. |
| ethyl alcohol | 50 g. |
| water, q.s.p. | 100 cc |

The results obtained by applying this setting lotion are excellent. The lotion not only imparts body and resilience to the hair but also its sheen. No powder is left in the comb when the hair is combed. A perfect coating is applied to the hair, and it therefore holds a set much better than conventional setting lotions.

EXAMPLE 61

| | |
|---|---|
| copolymer prepared according to Example 53 aminoethylpropanediol, q.s.p. 100% neutralization | 2 g. |
| Cetavlon (cetrimonium bromide) | 0.1 g. |
| ethyl alcohol q.s.p. | 50° |
| water, q.s.p. | 100 cc |

The results obtained are as good as in the case of Example 60.

EXAMPLE 62

| | |
|---|---|
| copolymer prepared as in Example 46 aminoethylpropanediol, q.s.p. 100% neutralization | 2 g. |
| Cetavlon (cetrimonium bromide) | 0.1 g. |
| ethyl alcohol q.s.p. | 50° |
| water, q.s.p. | 100 cc |

This lotion imparts holding power to the hair, and especially an attractive sheen. The hair is rendered soft to the touch and easy to untangle. This type of lotion is particularly suitable for sensitive or dried out hair.

EXAMPLE 63

A solution having the following composition is prepared:

| | |
|---|---|
| copolymer prepared as claimed in Example 47 aminoethylpropanediol, q.s.p. 100% neutralization | 2 g. |
| Cetavlon (cetrimonium bromide) | 0.1 g. |
| ethyl alcohol q.s.p. | 50° |
| water, q.s.p. | 100 cc |

The results obtained are as satisfactory as those described in Example 62.

EXAMPLE 64

An aerosol lacquer having the following composition is prepared:

| | |
|---|---|
| copolymer prepared in Example 45 2-amino-2-methyl-1,3-propanediol, q.s.p. 100% neutralization | 4 g. |
| perfume | 0.3 g. |
| absolute ethyl alcohol, q.s.p. | 100 g. |

25 g. of this solution are packaged in an aerosol bomb with 47 g. of the product sold under the trademark Freon 11 and 28 g. of the product sold under the trademark Freon 12.

EXAMPLE 65

An aerosol hair lacquer is produced by preparing a solution having the following composition:

| | |
|---|---|
| copolymer prepared as in Example 48 2-amino-2-methyl-1,3-propanediol, q.s.p. 100% neutralization | 8 g. |
| perfume | 0.25 g. |
| absolute ethyl alcohol q.s.p. | 100 g. |

25 g. of this solution are packaged in an aerosol bomb with 47 g. of the product sold under the trademark Freon 11 and 28 g. of the product sold under the trademark Freon 12.

A very strong lacquer results.

EXAMPLE 66

In order to prepare an aerosol hair lacquer, a solution having the following composition is prepared:

| | |
|---|---|
| copolymer prepared in accordance with Example 51 2-amino-2-methyl-1,3-propanediol, q.s.p. 100% neutralization | 4 g. |
| butyl myristate | 0.2 g. |
| perfume | 0.10 g. |
| absolute ethyl alcohol q.s.p. | 100 g. |

30 g. of this solution are packaged in an aerosol bomb with 35 g. of the product known under the trademark Freon 11 and 35 g. of the product sold under the trademark Freon 12.

When sprayed on the hair, a shiny lacquer having a strong lacquering power is obtained.

EXAMPLE 67

In order to produce an aerosol hair lacquer, a solution having the following composition is prepared:

| | |
|---|---|
| copolymer prepared according to Example 50 | 4 g. |
| absolute ethyl alcohol, q.s.p. | 100 g. |

25 g. of this solution are packaged in an aerosol bomb with 47 g. of the product sold under the trademark Freon 11 and 28 g. of the product sold under the trademark Freon 12.

When this is sprayed on the hair a tough, shiny, coating of lacquer is formed thereon.

EXAMPLE 68

The following composition forms a cream hair-setting lotion:

| | |
|---|---|
| copolymer prepared according | |

-continued

| to Example 53 aminomethylpropanediol, q.s.p. 100% neutralization pH 7 | 2 g. |
|---|---|
| Carbopol 940 (carboxypolymethylene) | 0.4 g. |
| triethanolamine | 0.5 g. |
| isopropyl alcohol | 20 g. |
| water, q.s.p. | 100 g. |

What is claimed is:

1. A copolymer consisting essentially of
   (1) 63–88% by weight vinyl acetate,
   (2) 5–15% by weight crotonic acid and
   (3) 5–25% by weight of a monomer selected from the group consisting of
   (i) vinylic ester of the formula $$R-COO-CH=CH_2$$

wherein R is a linear or branched chain hydrocarbon containing from 10 to 22 carbon atoms, and
   (ii) allylic or methallylic ester of the formula $$R'-COO-CH_2-\underset{R''}{C}=CH_2$$

wherein R' is a linear or branched chain hydrocarbon containing 10 to 22 carbon atoms and R'' is selected from the group consisting of hydrogen and methyl, wherein all of the monomers are copolymerized in the presence of a free radical catalyst, said copolymer having a molecular weight ranging between 10,000 and 300,000.

2. The copolymer of claim 1 wherein said vinylic ester is selected from the group consisting of vinyl laurate, vinyl palmitate, vinyl stearate, vinyl isostearate and vinyl behenate.

3. The copolymer of claim 1 wherein said allylic or methallylic ester is selected from the group consisting of allyl laurate, methallyl laurate, allyl stearate, methallyl stearate, allyl isostearate, methallyl isostearate and allyl behenate.

4. The copolymer of claim 1 having a molecular weight ranging between 15,000 and 160,000.

5. A copolymer consisting essentially of
   (1) 75–85% by weight vinyl acetate,
   (2) 5–15% by weight crotonic acid and
   (3) 5–15% by weight of an ether of the formula $$CH_2=CH--R''$$

wherein R'' is selected from the group consisting of ethyl, isopropyl, butyl, isobutyl and chloroethyl, wherein all of the monomers are copolymerized in the presence of a free radical catalyst, said copolymer having a molecular weight ranging between 10,000 and 300,000.

6. The copolymer of claim 5 wherein said ether is selected from the group consisting of isopropyl vinyl ether, isobutyl vinyl ether and chloroethyl vinyl ether.

7. The copolymer of claim 5 wherein the molecular weight ranges between 15,000 and 160,000.

8. A copolymer consisting essentially of
   (1) 50–90% by weight of a monomer selected from the group consisting of vinyl acetate, vinyl propionate, allyl acetate and vinyl butyrate,
   (2) 5–25% by weight of a monomer selected from the group consisting of 3-butenoic acid, 4-pentenoic acid, allylmalonic acid, allyloxyacetic acid and allylpropionic acid, and
   (3) 5–30% by weight of a monomer selected from the group consisting of 1-allyloxy-3-dodecyloxy-2-propanol, 1-allyloxy-3-dodecylthio-2-propanol, allyl oleate, stearyl vinyl ether, allyl stearate, crotyl laurate and allyl laurate, wherein all of the monomers are copolymerized in the presence of a free radical catalyst, said copolymer having a molecular weight ranging between 10,000 and 300,000.

9. The copolymer of claim 8 wherein the molecular weight ranges between 15,000 and 160,000.

* * * * *

UNITED STATES PATENT AND TRADEMARK OFFICE
CERTIFICATE OF CORRECTION

PATENT NO. : 4,129,711
DATED : December 12, 1978
INVENTOR(S) : Andre Viout and Regine Pasero It is certified that error appears in the above-identified patent and that said Letters Patent are hereby corrected as shown below:

<u>In the Heading</u> under "Related U.S. Application Data"

4th line, "July 28, 1967" should read

--July 25, 1967--.

<u>Claim 5</u>, line 5, the structural formula should read

-- $CH_2=CH-O-R''$ --.

*Signed and Sealed this*

*Sixth* Day of *November 1979*

[SEAL]

*Attest:*

RUTH C. MASON
*Attesting Officer*

LUTRELLE F. PARKER
*Acting Commissioner of Patents and Trademarks*